United States Patent
Lee et al.

(10) Patent No.: US 10,450,387 B2
(45) Date of Patent: Oct. 22, 2019

(54) MODIFIER, MODIFIED AND CONJUGATED DIENE-BASED POLYMER AND METHODS FOR PREPARING THEM

(71) Applicant: LG Chem, Ltd., Seoul (KR)

(72) Inventors: Seong Du Lee, Daejeon (KR); No Ma Kim, Daejeon (KR); He Seung Lee, Daejeon (KR); Hyoung Woo Lee, Daejeon (KR)

(73) Assignee: LG Chem, Ltd. (KR)

( * ) Notice: Subject to any disclaimer, the term of this patent is extended or adjusted under 35 U.S.C. 154(b) by 92 days.

(21) Appl. No.: 15/739,849

(22) PCT Filed: Jul. 21, 2017

(86) PCT No.: PCT/KR2017/007911
§ 371 (c)(1),
(2) Date: Dec. 26, 2017

(87) PCT Pub. No.: WO2018/105845
PCT Pub. Date: Jun. 14, 2018

(65) Prior Publication Data
US 2018/0371113 A1    Dec. 27, 2018

(30) Foreign Application Priority Data
Dec. 5, 2016   (KR) .................. 10-2016-0164584

(51) Int. Cl.
| | | |
|---|---|---|
| C08F 36/14 | (2006.01) | |
| C08F 8/30 | (2006.01) | |
| C08F 8/34 | (2006.01) | |
| C08F 8/42 | (2006.01) | |
| C08F 236/10 | (2006.01) | |
| C08K 5/544 | (2006.01) | |
| C08K 5/548 | (2006.01) | |
| C08C 19/25 | (2006.01) | |
| C07F 7/18 | (2006.01) | |
| C08C 19/20 | (2006.01) | |
| C08C 19/22 | (2006.01) | |
| C08C 19/44 | (2006.01) | |
| C08L 15/00 | (2006.01) | |
| C08F 212/08 | (2006.01) | |
| C08K 5/06 | (2006.01) | |
| C08K 5/17 | (2006.01) | |
| C08K 5/56 | (2006.01) | |

(52) U.S. Cl.
CPC ............ *C08C 19/25* (2013.01); *C07F 7/1804* (2013.01); *C07F 7/1876* (2013.01); *C08C 19/20* (2013.01); *C08C 19/22* (2013.01); *C08C 19/44* (2013.01); *C08F 212/08* (2013.01); *C08F 236/10* (2013.01); *C08K 5/06* (2013.01); *C08K 5/17* (2013.01); *C08K 5/544* (2013.01); *C08K 5/56* (2013.01); *C08L 15/00* (2013.01); C08F 2500/01 (2013.01); C08F 2500/04 (2013.01)

(58) Field of Classification Search
CPC ......... C08C 19/25; C08C 19/20; C08C 19/22; C08C 19/44; C07F 7/1804; C07F 7/1876; C08F 212/08; C08F 236/10; C08F 2500/01; C08F 2500/04; C08K 5/06; C08K 5/17; C08K 5/544; C08K 5/56; C08L 15/00
USPC ......................................................... 524/572
See application file for complete search history.

(56) References Cited

U.S. PATENT DOCUMENTS

| | | | |
|---|---|---|---|
| 4,397,994 A | 8/1983 | Takeuchi et al. | |
| 2013/0261252 A1* | 10/2013 | Nebhani | C08F 36/04 524/572 |
| 2014/0371383 A1* | 12/2014 | Hayata | C08K 3/36 524/548 |

(Continued)

FOREIGN PATENT DOCUMENTS

| | | |
|---|---|---|
| EP | 2644610 A1 | 10/2013 |
| EP | 2749575 A1 | 7/2014 |
| JP | 05072723 A  * | 3/1993 |

(Continued)

OTHER PUBLICATIONS

Pace, Vittorio, et al., "A Robust, Eco-Friendly Access to Secondary Thioamides through the Addition of Organolithium Reagents to Isothiocyanates in Cyclopentyl Methyl Ether (CPME)." Chemistry—A European Journal, 2015, vol. 21, No. 52, pp. 18966-18970.

(Continued)

*Primary Examiner* — Kelechi C Egwim
(74) *Attorney, Agent, or Firm* — Lerner, David, Littenberg, Krumholz & Mentlik, LLP

(57) ABSTRACT

The present invention relates to a modifier and a modified and conjugated diene-based polymer including a functional group derived therefrom, and more particularly, provides a modifier including a compound represented by Formula 1, a modified and conjugated diene-based polymer including a functional group derived from the modifier and a repeating unit derived from a conjugated diene-based monomer, and methods for preparing them.

[Formula 1]

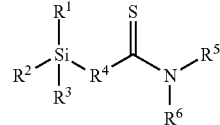

In Formula 1, the definition of each substituent is the same as defined in the description of the invention.

14 Claims, No Drawings

(56) References Cited

U.S. PATENT DOCUMENTS

2015/0299469 A1    10/2015    Takada et al.

FOREIGN PATENT DOCUMENTS

| JP | H0572723 A | 3/1993 |
|---|---|---|
| WO | 2013031599 A1 | 3/2013 |

OTHER PUBLICATIONS

Peng, Dongjie, et al., Phosphinite-Iminopyridine Iron Catalysts for Chemoselective Alkene Hydrosilylation. Journal of the American Chemical Society, 2013, Vo. 135, No. 51, pp. 19154-19166.

* cited by examiner

MODIFIER, MODIFIED AND CONJUGATED DIENE-BASED POLYMER AND METHODS FOR PREPARING THEM

CROSS-REFERENCE TO RELATED APPLICATIONS

The present application is a national phase entry under 35 U.S.C. § 371 of International Application No. PCT/KR2017/007911 filed on Jul. 21, 2017, which claims priority from Korean Patent Application No. 10-2016-0164584, filed on Dec. 5, 2016, the entire contents of which are incorporated herein by reference.

TECHNICAL FIELD

The present invention relates to a modifier and a modified and conjugated diene-based polymer including a functional group derived therefrom, and more particularly, to a modified and conjugated diene-based polymer having excellent tensile strength, abrasion resistance and viscoelasticity properties by including a functional group derived from a modifier having excellent affinity with an inorganic filler.

BACKGROUND ART

According to the recent demand for cars having a low fuel consumption ratio, a conjugated diene-based polymer having modulational stability represented by wet skid resistance as well as low rolling resistance, and excellent abrasion resistance and tensile properties is required as a rubber material for tires.

In order to reduce the rolling resistance of tires, there is a method of reducing hysteresis loss of vulcanized rubber, and rebound resilience at 50° C. to 80° C., tan δ, Goodrich heating, or the like is used as an evaluation index of the vulcanized rubber. That is, it is desirable to use a rubber material having high rebound resilience at the above temperature or a low tan δ value or Goodrich heating.

Natural rubbers, polyisoprene rubbers, or polybutadiene rubbers are known as rubber materials having low hysteresis loss, but these rubbers have a limitation of low wet skid resistance. Thus, recently, conjugated diene-based polymers or copolymers such as styrene-butadiene rubbers (hereinafter, referred to as "SBR") and butadiene rubbers of which cis content is controlled (hereinafter, referred to as "Low Cis BR"), are prepared by emulsion polymerization or solution polymerization to be used as rubbers for tires. Among these polymerization methods, the greatest advantage of the solution polymerization in comparison to the emulsion polymerization is that the vinyl structure content and the styrene content, which specify physical properties of the rubber, may be arbitrarily adjusted and its molecular weight and physical properties may be controlled via coupling or modification. Thus, the SBR prepared by the solution polymerization is widely used as a rubber material for tires because it is easy to change a structure of the finally prepared SBR or BR, and movement of chain terminals may be reduced and a coupling force with a filler such as silica and carbon black may be increased by coupling or modification of the chain terminals.

If the solution-polymerized SBR is used as the rubber material for tires, since a glass transition temperature of the rubber is increased by increasing the vinyl content in the SBR, physical properties such as running resistance and braking force, required for tires may be controlled, and fuel consumption may also be reduced by appropriately adjusting the glass transition temperature. The solution-polymerized SBR is prepared by using an anionic polymerization initiator and is being used by coupling or modifying the chain terminals of the polymer thus formed using various modifiers. For example, U.S. Pat. No. 4,397,994 discloses a method of coupling active anions of the chain terminals of a polymer obtained by polymerizing styrene-butadiene using alkyllithium which is a monofunctional initiator in a non-polar solvent, using a binder such as a tin compound.

Meanwhile, carbon black and silica are being used as a reinforcing filler of a tire tread, wherein, if the silica is used as the reinforcing filler, low-hysteresis loss may be and wet skid resistance may be improved. However, since the silica having a hydrophilic surface has a low affinity with a rubber in comparison to the carbon black having a hydrophobic surface, dispersibility may be poor, and thus, there is a need to use a separate silane coupling agent to improve the dispersibility or provide coupling between the silica and the rubber. Therefore, attempt of introducing a functional group having affinity or reactivity with silica into the terminal of a rubber molecule, is being performed, but its effect is insufficient. Accordingly, the development of rubbers having high affinity with silica is consistently required.

PRIOR ART DOCUMENT

Patent Document

U.S. Pat. No. 4,397,994

DISCLOSURE OF THE INVENTION

Technical Problem

The present invention has been devised in consideration of the above-mentioned problems, and objects of the present invention are to provide a modifier including a thioamide functional group which has excellent hydrophilicity in a molecule, a modified and conjugated diene-based polymer which has excellent affinity with an inorganic filler by including a functional group derived therefrom, and thus, has excellent tensile strength, abrasion resistance and viscoelasticity properties, and methods for preparing them.

Technical Solution

According to an embodiment of the present invention for solving the above-described tasks, there is provided a modified and conjugated diene-based polymer including a repeating unit derived from a conjugated diene-based monomer and a functional group derived from a modifier including a compound represented by the following Formula 1 at one terminal of the polymer:

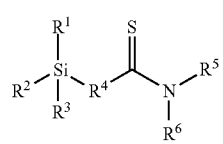

[Formula 1]

In Formula 1, $R^1$ to $R^3$ are each independently a monovalent hydrocarbon group of 1 to 30 carbon atoms, a heteroalkyl group of 1 to 30 carbon atoms, or a heterocyclic group of 3 to 30 carbon atoms, where at least one of $R^1$ to $R^3$ is the heteroalkyl group of 1 to 30 carbon atoms, or the heterocyclic group of 3 to 30 carbon atoms, $R^4$ is a divalent hydrocarbon group of 1 to 30 carbon atoms, $R^5$ and $R^6$ are each independently a monovalent hydrocarbon group of 1 to 30 carbon atoms, or $R^5$ and $R^6$ are combined with each other to form a saturated or unsaturated cyclic structure of 3 to 20 carbon atoms together with an adjacent N atom, where in case $R^5$ and $R^6$ form a cyclic structure, at least one heteroatom selected from the group consisting of O and S or $NR^{13}$ may be included, and $R^{13}$ is a monovalent hydrocarbon group of 1 to 30 carbon atoms, or a silyl group which is mono-, di- or tri-substituted with a monovalent hydrocarbon group of 1 to 30 carbon atoms.

In addition, the present invention provides a method for preparing a modified and conjugated diene-based polymer, including a step of polymerizing conjugated diene-based monomers, or an aromatic vinyl-based monomer and a conjugated diene-based monomer in the presence of an organometal compound in a hydrocarbon solvent to prepare an active polymer which is combined with an organometal (S1); and a step of reacting the active polymer with a modifier including a compound represented by the following Formula 1 (S2):

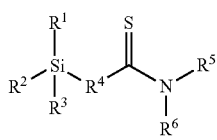

[Formula 1]

In Formula 1, the definition of each substituent is the same as defined above.

In addition, the present invention provides a modifier including the compound represented by Formula 1, and a preparation method thereof.

Advantageous Effects

If a conjugated diene-based polymer is modified from a modifier containing a thioamide functional group which has excellent hydrophilicity in a molecule and thus, having excellent affinity with an inorganic filler, a functional group derived from the modifier is included at one terminal of the polymer, and thus, the preparation of a modified and conjugated diene-based polymer having excellent affinity with an inorganic filler may be achieved, and the modified and conjugated diene-based polymer thus prepared has effects of achieving excellent tensile strength, abrasion resistance and viscoelasticity properties.

BEST MODE FOR CARRYING OUT THE INVENTION

Hereinafter, the present invention will be described in more detail in order to assist the understanding of the present invention.

It will be understood that words or terms used in the description and claims of the present invention shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

The modified and conjugated diene-based polymer according to the present invention includes a repeating unit derived from a conjugated diene-based monomer and may include a functional group derived from a modifier including a compound represented by the following Formula 1 at one terminal of the polymer:

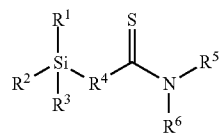

[Formula 1]

In Formula 1, $R^1$ to $R^3$ may be each independently a monovalent hydrocarbon group of 1 to 30 carbon atoms, a heteroalkyl group of 1 to 30 carbon atoms, or a heterocyclic group of 3 to 30 carbon atoms, where at least one of $R^1$ to $R^3$ may be the heteroalkyl group of 1 to 30 carbon atoms, or the heterocyclic group of 3 to 30 carbon atoms, $R^4$ may be a divalent hydrocarbon group of 1 to 30 carbon atoms, $R^5$ and $R^6$ may be each independently a monovalent hydrocarbon group of 1 to 30 carbon atoms, or $R^5$ and $R^6$ may be combined with each other to form a saturated or unsaturated cyclic structure of 3 to 20 carbon atoms together with an adjacent N atom, where in case $R^5$ and $R^6$ form a cyclic structure, at least one heteroatom selected from the group consisting of O and S or $NR^{13}$ may be included, and $R^{13}$ may be a monovalent hydrocarbon group of 1 to 30 carbon atoms, or a silyl group which is mono-, di- or tri-substituted with a monovalent hydrocarbon group of 1 to 30 carbon atoms.

In a particular embodiment, in Formula 1, $R^1$ to $R^3$ may be each independently a monovalent hydrocarbon group of 1 to 20 carbon atoms, a heteroalkyl group of 1 to 20 carbon atoms, or a heterocyclic group of 3 to 20 carbon atoms, at least one of $R^1$ to $R^3$ may be the heteroalkyl group of 1 to 20 carbon atoms, or the heterocyclic group of 3 to 20 carbon atoms, $R^4$ may be a divalent hydrocarbon group of 1 to 20 carbon atoms, $R^5$ and $R^6$ may be each independently a monovalent hydrocarbon group of 1 to 12 carbon atoms, or $R^5$ and $R^6$ may be combined with each other to form a saturated or unsaturated cyclic structure of 3 to 12 carbon atoms together with an adjacent N atom, where if $R^5$ and $R^6$ form a cyclic structure, at least one heteroatom selected from the group consisting of 0 and S or $NR^{13}$ may be included, and $R^{13}$ may be a monovalent hydrocarbon group of 1 to 20 carbon atoms, or a mono-, di- or tri-substituted silyl group with a monovalent hydrocarbon group of 1 to 20 carbon atoms.

In the present invention, the term "monovalent hydrocarbon group" may mean a monovalent atomic group in which carbon and hydrogen are bonded such as a monovalent alkyl group, alkenyl group, alkynyl group, cycloalkyl group, cycloalkyl group containing at least one unsaturated bond, and aryl group.

In the present invention, the term "divalent hydrocarbon group" may mean a divalent atomic group in which carbon and hydrogen are bonded such as a divalent alkylene group, alkenylene group, alkynylene group, cycloalkylene group, cycloalkylene group containing at least one unsaturated bond and arylene group.

In the present invention, the term "heteroalkyl group" may mean an alkyl group in which a carbon atom (including a terminal carbon atom) in the alkyl group is substituted with at least one heteroatom. Particularly, the heteroalkyl group may include all of an alkoxy group, an ether group, an amino group, a thioalkoxy group and a thioether group.

In the present invention, the term "heterocyclic group" may include all of a cycloalkyl group and an aryl group, in which a carbon atom in the cycloalkyl group or the aryl group is substituted with at least one heteroatom.

According to an embodiment of the present invention, the compound represented by Formula 1 may be at least one selected from compounds represented by the following Formulae 1-1 to 1-4:

[Formula 1-1]

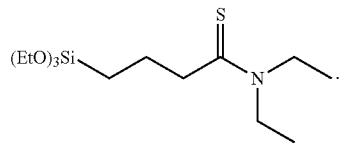

N,N-diethyl-4-(triethoxysilyl)butanethioamide

[Formula 1-2]

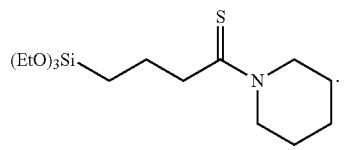

1-(piperidin-1-yl)-4-(triethoxysilyl)butane-1-thione

[Formula 1-3]

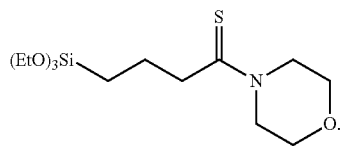

1-morpholino-4-(triethoxysilyl)butane-1-thione

[Formula 1-4]

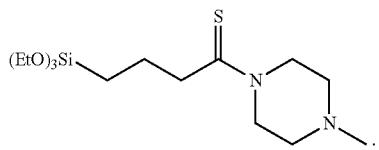

1-(4-methylpiperazin-1-yl)-4-(triethoxysilyl)butane-1-thione

In Formulae 1-1 to 1-4, Et is an ethyl group.

As described above, according to the present invention, if a conjugated diene-based polymer is modified from a modifier including a compound represented by Formula 1 which contains a thioamide functional group which has excellent hydrophilicity in a molecule and thus having excellent affinity with an inorganic filler, the functional group derived from the modifier is included at one terminal of the polymer, and thus, the preparation of a modified and conjugated diene-based polymer having excellent affinity with an inorganic filler may be achieved. The modified and conjugated diene-based polymer thus prepared has effects of having excellent tensile strength, abrasion resistance and viscoelasticity properties.

The repeating unit derived from the conjugated diene-based monomer may mean a repeating unit constituted during the polymerization of a conjugated diene-based monomer, and the conjugated diene-based monomer may be, for example, at least one selected from the group consisting of 1,3-butadiene, 2,3-dimethyl-1,3-butadiene, piperylene, 3-butyl-1,3-octadiene, isoprene, 2-phenyl-1,3-butadiene and 2-halo-1,3-butadiene (halo means a halogen atom).

Meanwhile, the modified and conjugated diene-based copolymer may be a copolymer further including, for example, a repeating unit derived from an aromatic vinyl monomer together with the repeating unit derived from the conjugated diene-based monomer.

The repeating unit derived from the aromatic vinyl monomer may mean a repeating unit constituted during the polymerization of the aromatic vinyl monomer, and the aromatic vinyl monomer may include, for example, at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene and 1-vinyl-5-hexylnaphthalene.

If the modified and conjugated diene-based polymer is a copolymer including a repeating unit derived from an aromatic vinyl monomer, the modified and conjugated diene-based polymer may include the repeating unit derived from a conjugated diene-based monomer from 50 to 95 wt %, from 60 to 85 wt %, or from 60 to 80 wt % and may include the repeating unit derived from an aromatic vinyl monomer from 5 to 50 wt %, from 15 to 40 wt %, or from 20 to 40 wt %. Within the ranges, effects of excellent rolling resistance, wet traction and abrasion resistance may be achieved.

Meanwhile, the modified and conjugated diene-based copolymer may be, for example, a copolymer further including a repeating unit derived from a modified monomer containing a compound represented by Formula 2 below together with the repeating unit derived from the conjugated diene-based monomer.

[Formula 2]

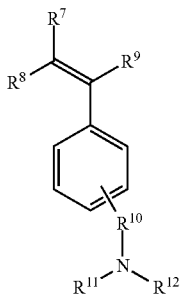

In Formula 2, $R^7$, $R^8$ and $R^9$ may be each independently hydrogen, or a monovalent hydrocarbon group of 1 to 20 carbon atoms, $R^{10}$ may be a single bond, a divalent hydrocarbon group of 1 to 20 carbon atoms, or a hetero alkylene group containing at least one heteroatom selected from the group consisting of O and S or $NR^{14}$, $R^{11}$ and $R^{12}$ may be each independently a monovalent hydrocarbon group of 1 to 30 carbon atoms, or a silyl group which is mono-, di- or tri-substituted with a monovalent hydrocarbon group of 1 to 30 carbon atoms, or $R^{11}$ and $R^{12}$ may be combined with each other to form a saturated or unsaturated cyclic structure of 3 to 20 carbon atoms together with an adjacent N atom, where in case $R^{11}$ and $R^{12}$ form a cyclic structure, at least one heteroatom selected from the group consisting of O and S or $NR^{15}$ may be included, and $R^{14}$ and $R^{15}$ may be each independently a monovalent hydrocarbon group of 1 to 30 carbon atoms, or a silyl group which is mono-, di- or tri-substituted with a monovalent hydrocarbon group of 1 to 30 carbon atoms.

Particularly, the compound represented by Formula 2 may be at least one selected from the group consisting of N,N-dimethylvinylbenzylamine, N,N-diethylvinylbenzylamine, N,N-dipropylvinylbenzylamine, N,N-dibutylvinylbenzylamine, N,N-diphenylvinylbenzylamine, 2-dimethylaminoethylstyrene, 2-diethylaminoethylstyrene, 2-bis(trimethylsilyl)aminoethylstyrene, 1-(4-N,N-dimethylaminophenyl)-1-phenylethylene, N,N-dimethyl-2-(4-vinylbenzyloxy)ethylamine, N,N,N'-trimethyl-N'-(4-vinylbenzyl)ethane-1,2-diamine, N,N-dimethyl-2-((4-vinylbenzyl)thio)ethylamine, 4-(2-pyrrolidinoethyl)styrene, 4-(2-piperidinoethyl)styrene, 4-(2-hexamethyleneiminoethyl)styrene, 4-(2-morpholinoethyl)styrene, 4-(2-thiadinoethyl)styrene, 4-(2-N-methylpiperazinoethyl)styrene, 1-((4-vinylphenoxy)methyl)pyrrolidine, 1-(4-vinylbenzyloxymethyl)pyrrolidine, 1-((4-vinylbenzyl)thiomethyl)pyrrolidine, and N-methyl-1-(pyrrolidine-1-yl)-N-(4-vinylbenzyl)methylamine.

The repeating unit derived from the modified monomer containing the compound represented by Formula 2 may, for example, be included in the terminal of a polymer in which the substitution of the functional group derived from the modifier including the compound represented by Formula 1 occurs. In this case, by end-capping the terminal of the conjugated diene-based polymer with the repeating unit derived from the modified monomer, excellent affinity with a filler and effects of excellent bonding efficiency during modification reaction or coupling reaction with a modifier may be attained.

According to an embodiment of the present invention, the copolymer may be a random copolymer, and in this case, effects of excellent balance between each of physical properties may be achieved. The random copolymer may mean the arrangement of repeating units constituting the copolymer in disorder.

The modified and conjugated diene-based polymer according to an embodiment of the present invention may have a number average molecular weight (Mn) of 1,000 g/mol to 2,000,000 g/mol, 10,000 g/mol to 1,000,000 g/mol, or 100,000 g/mol to 500,000 g/mol. Within this range, effects of excellent rolling resistance and wet traction may be obtained. In another embodiment, the modified and conjugated diene-based polymer may have molecular weight distribution (Mw/Mn) of 1 to 5, 1.3 to 4, or 1.5 to 3, and within this range, effects of excellent balance between physical properties may be obtained.

In another embodiment, the money viscosity of the modified and conjugated diene-based polymer at 100° C. may be 20 or more, from 30 to 150, or from 40 to 120, and within this range, effects of excellent processability and productivity may be obtained.

In addition, the vinyl content of the modified and conjugated diene-based polymer may be 18 wt % or more, 25 wt % or more, or from 30 wt % to 70 wt %, and within this range, a glass transition temperature may be controlled in an appropriate range, and effects of excellent rolling resistance, wet traction and a low consumption ratio may be obtained. Here, the vinyl content may represent the amount of not 1,4-added but 1,2-added conjugated diene-based monomer based on 100 wt % of the total amount of the conjugated diene-based polymer composed of a vinyl group-containing monomer and an aromatic vinyl-based monomer.

Meanwhile, in the present invention, the term "derived repeating unit" and "derived functional group" may represent a component or a structure derived from a material, or the material itself.

A method for preparing a modified and conjugated diene-based polymer according to the present invention may include a step of polymerizing conjugated diene-based monomers, or an aromatic vinyl-based monomer and a conjugated diene-based monomer in the presence of an organometal compound in a hydrocarbon solvent to prepare an active polymer which is combined with an organometal (S1); and a step of reacting the active polymer with a modifier including a compound represented by the following Formula 1 (S2):

[Formula 1]

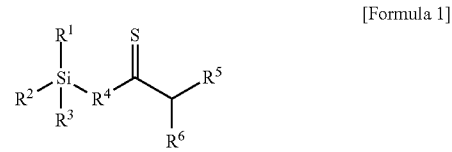

The definition of each substituent in Formula 1 is the same as defined above.

The hydrocarbon solvent is not specifically limited and may be, for example, at least one selected from the group consisting of n-pentane, n-hexane, n-heptane, isooctane, cyclohexane, toluene, benzene and xylene.

According to an embodiment of the present invention, the compound represented by Formula 1 may be used in an amount of 0.01 mol to 10 mol, 0.05 mol to 8 mol, or 0.1 mol to 4 mol based on 1 mol of the organometal compound.

In another embodiment, the amount of the compound represented by Formula 1 may be controlled and used such that the number of the active polymer prepared in step (S1) coincides with the number of the heteroalkyl group of 1 to 30 carbon atoms or the heterocyclic group of 3 to 30 carbon atoms among R1 to R3, which is substituted at a silyl group present in the compound represented by Formula 1, particularly, may be used such that from 20% to 70%, from 40% to 70%, or from 45% to 55% of the active polymer based on the number of the active polymer prepared in step (S1) coincides with the number of the heteroalkyl group of 1 to 30 carbon atoms or the heterocyclic group of 3 to 30 carbon atoms among R1 to R3, which is substituted at a silyl group present in the compound represented by Formula 1.

According to an embodiment of the present invention, the compound represented by Formula 1 may be used in an amount of 0.01 mmol to 10 mmol, 0.1 mmol to 8 mmol, or 0.5 mmol to 5 mmol based on 100 g of the monomer represented by Formula 1.

According to an embodiment of the present invention, the organometal compound may be used from 0.01 mmol to 10 mmol, from 0.05 mmol to 5 mmol, from 0.1 mmol to 2 mmol, or from 0.1 mmol to 1 mmol based on 100 g of the total monomers.

The organometal compound may be, for example, at least one selected from the group consisting of methyllithium, ethyllithium, propyllithium, n-butyllithium, s-butyllithium, t-butyllithium, hexyllithium, n-decyllithium, t-octyllithium, phenyllithium, 1-naphthyl lithium, n-eicosyl lithium, 4-butylphenyl lithium, 4-tolyl lithium, cyclohexyl lithium, 3,5-di-n-heptylcyclohexyl lithium, 4-cyclopentyl lithium, naphthyl sodium, naphthyl potassium, lithium alkoxide, sodium alkoxide, potassium alkoxide, lithium sulfonate, sodium sulfonate, potassium sulfonate, lithium amide, sodium amide, potassium amide, and lithium isopropylamide.

The polymerization of step (S1) may be conducted by including a modification monomer including a compound represented by the following Formula 2:

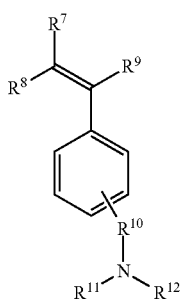

[Formula 2]

In Formula 2, the definition on each substituent is the same as defined above.

The modification monomer including the compound represented by Formula 2 may be, for example, injected with the conjugated diene-based monomer, or the aromatic vinyl-based monomer and the conjugated diene-based monomer, simultaneously, or may be separately injected after completing the injection of the conjugated diene-based monomer, or the aromatic vinyl-based monomer and the conjugated diene-based monomer. If the modification monomer including the compound represented by Formula 2 is injected after completing the injection of the conjugated diene-based monomer, or the aromatic vinyl-based monomer and the conjugated diene-based monomer, end-capping effect of the terminal of the active polymer is achieved.

Meanwhile, the polymerization of step (S1) may be conducted by adding a polar additive, and the polar additive may be added in an amount of 0.001 g to 50 g, 0.001 g to 2 g, 0.05 g to 1 g, or 0.08 g to 0.5 g based on 100 g of the total monomers. The polar additive may be at least one selected from the group consisting of tetrahydrofuran, ditetrahydrofurylpropane, diethyl ether, cycloamal ether, dipropyl ether, ethylene methyl ether, ethylene dimethyl ether, diethyl glycol, dimethyl ether, tert-butoxy ethoxy ethane, bis(3-dimethylaminoethyl) ether, (dimethylaminoethyl) ethyl ether, trimethylamine, triethylamine, tripropylamine, and tetramethylethylenediamine, preferably, triethylamine or tetramethylethylenediamine, and may be the same as or different from a polar additive which may be injected during preparing the aminosilane-based compound. If the polar additive is included, and in case of copolymerizing a conjugated diene-based monomers, or a conjugated diene-based monomer and an aromatic vinyl-based monomer, the difference of the reaction rates therebetween may be compensated, thereby attaining easy formation of a random copolymer.

The polymerization of step (S1) may be, for example, an anionic polymerization, and particularly, may be a living anionic polymerization in which an anionic active part is formed at the polymerization terminal through a propagation reaction by anions. In addition, the polymerization of step (S1) may be conducted by a polymerization with heating, a polymerization at a constant temperature, or an adiabatic polymerization. Here, the adiabatic polymerization means a polymerization method including a step of polymerizing using self-generated heat of reaction without optionally applying heat after adding the organometal compound, and the polymerization with heating means a polymerization method by which the temperature of a polymer is increased by optionally applying heat after adding the organometal compound. The polymerization at a constant temperature means a polymerization method by which the temperature of a polymer is kept constant by optionally applying heat or taking heat after adding the organometal compound. In addition, the polymerization of step (S1) may be conducted in a temperature range of −20° C. to 200° C., −20° C. to 150° C., 0° C. to 120° C., or 50° C. to 100° C.

The active polymer prepared by step (S1) may mean a polymer in which a polymer anion and an organometal cation are bonded.

According to an embodiment of the present invention, the molar ratio of the modifier including the compound represented by Formula 1 and the organometal compound may be from 1:0.1 to 1:10, and within this range, a modification reaction of the optimized performance may be conducted, and a conjugated diene-based polymer with high modification rate may be obtained.

The reaction of step (S2) is a modification reaction for introducing a functional group derived from the modifier into an active polymer, and may be conducted at from 0° C. to 90° C. for 1 minute to 5 hours.

In addition, according to an embodiment of the present invention, the preparation method of the modified and conjugated diene-based polymer may be conducted by a batch-type polymerization method or a continuous type polymerization method including at least one reactor.

The preparation method of the modified and conjugated diene-based polymer may further include at least one step of recovering and drying of solvents and unreacted monomers after step (S2), if needed.

The modifier according to the present invention may include a compound represented by the following Formula 1:

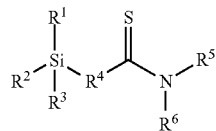

[Formula 1]

The definition of each substituent in Formula 1 is the same as defined above.

The modifier of the present invention includes a thioamide functional group which has excellent hydrophilicity in a molecule, and affinity with an inorganic filler, particularly, a silica-based filler is excellent, and accordingly, effect of increasing dispersibility between a modified polymer from the modifier and a filler is obtained.

According to the present invention, in order to prepare a modifier including the compound represented by Formula 1, there is provided a method for preparing a modifier including a step of thionating a compound represented by the following Formula 3 to prepare a compound represented by the following Formula 4 (S3); and a step of reacting the compound represented by the following Formula 4 which is prepared in step (S3) and a compound represented by the following Formula 5 (S4):

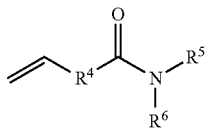

[Formula 3]

in Formula 3, R[4'] may be a divalent hydrocarbon group of 1 to 28 carbon atoms, R[5] and R[6] may be each independently a monovalent hydrocarbon group of 1 to 30 carbon atoms, or R[5] and R[6] may be combined with each other to form a saturated or unsaturated cyclic structure of 3 to 20 carbon atoms together with an adjacent N atom, where in case R[5] and R[6] form a cyclic structure, at least one heteroatom selected from the group consisting of O and S or NR[13] may be included, and R[13] may be a monovalent hydrocarbon group of 1 to 30 carbon atoms, or a silyl group which is mono-, di- or tri-substituted with a monovalent hydrocarbon group of 1 to 30 carbon atoms,

[Formula 4]

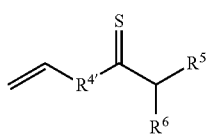

in Formula 4, R[4'] may be a divalent hydrocarbon group of 1 to 28 carbon atoms, R[5] and R[6] may be each independently a monovalent hydrocarbon group of 1 to 30 carbon atoms, or R[5] and R[6] may be combined with each other to form a saturated or unsaturated cyclic structure of 3 to 20 carbon atoms together with an adjacent N atom, where in case R[5] and R[6] form a cyclic structure, at least one heteroatom selected from the group consisting of O and S or NR[13] may be included, and R[13] may be a monovalent hydrocarbon group of 1 to 30 carbon atoms, or a silyl group which is mono-, di- or tri-substituted with a monovalent hydrocarbon group of 1 to 30 carbon atoms,

[Formula 5]

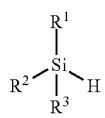

in Formula 5, R[1] to R[3] are each independently a monovalent hydrocarbon group of 1 to 30 carbon atoms, a heteroalkyl group of 1 to 30 carbon atoms, or a heterocyclic group of 3 to 30 carbon atoms, where at least one of R[1] to R[3] may be the heteroalkyl group of 1 to 30 carbon atoms, or the heterocyclic group of 3 to 30 carbon atoms.

Particularly, in Formulae 3 and 4, R[4'] may be a divalent hydrocarbon group of 1 to 18 carbon atoms, R[5] and R[6] may be each independently a monovalent hydrocarbon group of 1 to 12 carbon atoms, or R[5] and R[6] may be combined with each other to form a saturated or unsaturated cyclic structure of 3 to 12 carbon atoms together with an adjacent N atom, if R[5] and R[6] forms a cyclic structure, at least one heteroatom selected from the group consisting of O and S or NR[13] may be included, and R[13] may be a monovalent hydrocarbon group of 1 to 20 carbon atoms, or a mono-, di-, or tri-substituted silyl group with a monovalent hydrocarbon group of 1 to 20 carbon atoms.

More particularly, the compound represented by Formula 3 may be N,N-diethyl-3-butenamide, 1-(piperidin-1-yl)-but-3-en-1-one, 1-morpholinobut-3-en-1-one, or 1-(4-methyl-piperazin-1-yl)-but-3-en-1-one.

In addition, particularly, in Formula 5, R[1] to R[3] may be each independently a monovalent hydrocarbon group of 1 to 20 carbon atoms, a heteroalkyl group of 1 to 20 carbon atoms, or a heterocyclic group of 3 to 20 carbon atoms, where at least one of R[1] to R[3] may be definitely a heteroalkyl group of 1 t 20 carbon atoms, or a heterocyclic group of 3 to 20 carbon atoms.

According to an embodiment of the present invention, the thionation of step (S3) may be conducted by adding a sulfur source, and the sulfur source may be a compound which may provide a sulfur atom for transforming an amide functional group into a thioamide functional group, particularly, a Lawesson reagent (2,4-bis(4-methoxyphenyl)-1,3-dithia-2,4-diphosphetane).

In addition, according to an embodiment of the present invention, the sulfur source for the thionation of step (S3) may be added in a molar ratio of 1:0.1 to 10, 1:0.1 to 5, or 1:0.5 to 3 based on 1 mol of the compound represented by Formula 3, and within this range, effects of minimizing side-reactions and excellent yield may be achieved.

Meanwhile, the thionation of step (S3) may be conducted in a reaction temperature of, for example, 0° C. to 120° C., 10° C. to 100° C., or 20° C. to 80° C., and within this range, increasing effects of a yield of a reaction may be achieved.

In another embodiment, the thionation of step (S3) may be conducted for 10 minutes to 24 hours, 1 hour to 10 hours, or 2 hours to 8 hours, and within this range, increasing effects of a yield of a reaction may be achieved.

In addition, the thionation of step (S3) may be conducted in an organic solvent, and particular example of the organic solvent may be at least one selected from the group consisting of tetrahydrofuran (THF), benzene, toluene, dioxane and dichloromethane.

According to an embodiment of the present invention, the reaction of step (S4) may be hydrosilylation of the compound represented by Formula 4 and the compound represented by Formula 5, and may be conducted in the presence of a metal catalyst. The metal catalyst may be a metal catalyst which may provide a metallocycle reaction mechanism for conducting hydrosilylation, particularly, a metal catalyst which may conduct oxidative addition and reductive elimination at the same time. According to an embodiment of the present invention, the metal catalyst may be dicobalt octacarbonyl.

In addition, according to an embodiment of the present invention, the metal catalyst for the reaction of step (S4) may be present in a molar ratio of 1:0.01 to 10, 1:0.02 to 5, or 1:0.03 to 2 based on 1 mol of the compound represented by Formula 4, and within this range, effects of minimizing side-reactions and excellent yield may be achieved.

Further, according to an embodiment of the present invention, in the reaction of step (S4), the molar ratio of the compound represented by Formula 4 and the compound represented by Formula 5 may be 1:0.1 to 10, 1:0.1 to 5, or 1:0.5 to 3 based on 1 mol of the compound represented by Formula 4, and within this range, effects of minimizing side-reactions and excellent yield may be achieved.

Meanwhile, the reaction of step (S4) may be conducted in a reaction temperature of, for example, 0° C. to 100° C., 10° C. to 80° C., or 20° C. to 60° C., and within this range, increasing effects of a yield of a reaction may be obtained.

In another embodiment, the reaction of step (S4) may be conducted for 10 minutes to 24 hours, 1 hour to 12 hours, or 2 hours to 10 hours, and within this range, increasing effects of a yield of a reaction may be obtained.

In addition, the reaction of step (S4) may be conducted without solvent or in an organic solvent. If the reaction is conducted in the organic solvent, the organic solvent may be at least one selected from the group consisting of tetrahydrofuran (THF), benzene, toluene, dioxane and dichloromethane.

According to an embodiment of the present invention, a modifier including the compound represented by Formula 1 may be prepared via the reaction of step (S4).

According to the present invention, there is provided a rubber composition including the modified and conjugated diene-based polymer.

The rubber composition may include the modified and conjugated diene-based polymer in an amount of 10 wt % or more, 10 wt % to 100 wt %, or 20 wt % to 90 wt %, and within this range, mechanical properties such as tensile strength and abrasion resistance are excellent, and effects of excellent balance between each of the physical properties may be achieved.

In addition, the rubber composition may further include other rubber components, if necessary, in addition to the modified and conjugated diene-based polymer, and, in this case, the rubber component may be included in an amount of 90 wt % or less based on the total amount of the rubber composition. Specifically, the rubber composition may include the other rubber component in an amount of 1 part by weight to 900 parts by weight based on 100 parts by weight of the modified and conjugated diene-based polymer.

The rubber component may be a natural rubber or a synthetic rubber, and the rubber component may be, for example, a natural rubber (NR) including cis-1,4-polyisoprene; a modified natural rubber which is obtained by modifying or purifying a common natural rubber, such as an epoxidized natural rubber (ENR), a deproteinized natural rubber (DPNR), and a hydrogenated natural rubber; and a synthetic rubber such as a styrene-butadiene copolymer (SBR), a polybutadiene (BR), a polyisoprene (IR), a butyl rubber (IIR), an ethylene-propylene copolymer, a polyisobutylene-co-isoprene, a neoprene, a poly(ethylene-co-propylene), a poly(styrene-co-butadiene), a poly(styrene-co-isoprene), a poly(styrene-co-isoprene-co-butadiene), a poly(isoprene-co-butadiene), a poly(ethylene-co-propylene-co-diene), a polysulfide rubber, an acryl rubber, a urethane rubber, a silicone rubber, an epichlorohydrin rubber, a butyl rubber, a halogenated butyl rubber, and any one or a mixture of at least two thereof may be used.

The rubber composition may include 0.1 parts by weight to 200 parts by weight, or 10 parts by weight to 120 parts by weight of a filler based on 100 parts by weight of the modified and conjugated diene-based polymer of the present invention. The filler may particularly be a silica-based filler, more particularly, wet silica (hydrated silicate), dry silica (anhydrous silicate), calcium silicate, aluminum silicate, or colloid silica. Preferably, the filler may be wet silica which has the most significant improving compatible effects of the improving effect of destruction characteristics and wet grip characteristics. In addition, the rubber composition may further include a carbon black-based filler, if needed.

In another embodiment, if silica is used as the filler, a silane coupling agent may be used together for the improvement of reinforcing and low exothermic properties.

The silane coupling agent may particularly include bis(3-triethoxysilylpropyl)tetrasulfide, bis(3-triethoxysilylpropyl) trisulfide, bis(3-triethoxysilylpropyl)disulfide, bis(2-triethoxysilylethyl)tetrasulfide, bis(3-trimethoxysilylpropyl) tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyltetrasulfide, 3-triethoxysilylpropyl-N,N-dimethylthiocarbamoyltetrasulfide, 2-triethoxysilylethyl-N,N-dimethylthiocarbamoyltetrasulfide, 3-trimethoxysilylpropylbenzothiazolyltetrasulfide, 3-triethoxysilylpropylbenzolyltetrasulfide, 3-triethoxysilylpropylmethacrylatemonosulfide, 3-trimethoxysilylpropylmethacrylatemonosulfide, bis(3-diethoxymethylsilylpropyl) tetrasulfide, 3-mercaptopropyldimethoxymethylsilane, dimethoxymethylsilylpropyl-N,N-dimethylthiocarbamoyltetrasulfide, or dimethoxymethylsilylpropylbenzothiazolyltetrasulfide, and any one or a mixture of at least two thereof may be used. More particularly, bis(3-triethoxysilylpropyl)polysulfide or 3-trimethoxysilylpropylbenzothiazyltetrasulfide may be used in consideration of the improving effect of reinforcing properties.

In addition, in the rubber composition according to an embodiment of the present invention, a modified and conjugated diene-based polymer in which a functional group having high affinity with silica is introduced into an active part is used as a rubber component, and the mixing amount of a silane coupling agent may be smaller than a common case.

In particular, the silane coupling agent may be used in an amount of 1 part by weight to 20 parts by weight, or 5 parts by weight to 15 parts by weight based on 100 parts by weight of the silica. With the amount used in the above range, effects as a coupling agent may be sufficiently exhibited, and the gelation of a rubber component may be prevented.

The rubber composition according to an embodiment of the present invention may be sulfur crosslinkable, and may further include a vulcanizing agent. The vulcanizing agent may be particularly a sulfur powder and may be included in an amount of 0.1 parts by weight to 10 parts by weight based on 100 parts by weight of a rubber component. With the amount used in the above range, elasticity and strength required for a vulcanized rubber composition may be secured, and at the same time, a low fuel consumption ratio may be attained.

The rubber composition according to an embodiment of the present invention may further include various additives used in a common rubber industry in addition to the above-described components, particularly, a vulcanization accelerator, a process oil, a plasticizer, an antiaging agent, a scorch preventing agent, a zinc white, stearic acid, a thermosetting resin, or a thermoplastic resin.

The vulcanization accelerator may particularly include thiazole-based compounds such as 2-mercaptobenzothiazole (M), dibenzothiazyldisulfide (DM), and N-cyclohexyl-2-benzothiazylsulfenamide (CZ), or guanidine-based compounds such as diphenylguanidine (DPG). The vulcanization accelerator may be included in an amount of 0.1 parts by weight to 5 parts by weight based on 100 parts by weight of the rubber component.

The process oil acts as a softener in a rubber composition and may particularly include a paraffin-based, naphthene-based, or aromatic compound. More particularly, an aromatic process oil may be used in consideration of tensile strength and abrasion resistance, and a naphthene-based or paraffin-based process oil may be used in consideration of hysteresis loss and properties at low temperature. The process oil may be included in an amount of 100 parts by weight or less based on 100 parts by weight of the rubber component. Within the above-described range, the deterioration of tensile strength and low exothermic properties (low fuel consumption ratio) of the vulcanized rubber may be prevented.

The antiaging agent may particularly include N-isopropyl-N'-phenyl-p-phenylenediamine, N-(1,3-dimethylbutyl)-

N'-phenyl-p-phenylenediamine, 6-ethoxy-2,2,4-trimethyl-1,2-dihydroquinoline, or a condensate of diphenylamine and acetone at a high temperature. The antiaging agent may be used in an amount of 0.1 parts by weight to 6 parts by weight based on 100 parts by weight of the rubber component.

The rubber composition according to an embodiment of the present invention may be obtained by mulling using a mulling apparatus such as a banbury mixer, a roll, and an internal mixer according to a mixing prescription. In addition, a rubber composition having low exothermic properties and good abrasion resistance may be obtained by a molding process and a subsequent a vulcanization process.

Therefore, the rubber composition may be useful for the manufacture of each member of a tire such as a tire tread, an under tread, a side wall, a carcass coating rubber, a belt coating rubber, a bead filler, a chafer, and a bead coating rubber, or to the manufacture of rubber products in various industries such as a dustproof rubber, a belt conveyor, and a hose.

Meanwhile, when measuring the rubber composition, for example, with 10 Hz via DMA, a Tan δ value at 0° C. (Tan δ at 0° C.) may be from 0.6 to 1, or from 0.8 to 1, and within this range, effects of excellent wet traction and wet resistance may be obtained.

In addition, when measuring the rubber composition, for example, with 10 Hz via DMA, a Tan δ value at 60° C. (Tan δ at 60° C.) may be from 0.15 to 0.1, or from 0.13 to 0.11, and within this range, effects of excellent rolling resistance and rotation resistance may be obtained.

Further, there is provided in the present invention, a tire manufactured using the rubber composition.

The tire may include a tire or a tire tread.

BEST MODE FOR CARRYING OUT THE INVENTION

Hereinafter, the present invention will be explained in particular referring to embodiments. However, the following embodiments are only for the illustration of the present invention, and the scope of the present invention is not limited thereto.

PREPARATION EXAMPLES

Preparation Example 1: Preparation of Compound of Formula 1-1 Below

Thionation Process

A 1 L reactor provided with a stirrer and a jacket was dried with nitrogen in advance, and 0.1 mol of N,N-diethyl-3-butenamide, 0.05 mol of a Lawesson reagent (2,4-bis(4-methoxyphenyl)-1,3-dithia-2,4-diphosphetane), and 150 ml of tetrahydrofuran (THF) were injected thereto one by one and stirred for mixing. Then, the temperature of the reactor was elevated to 55° C., followed by stirring for 4 hours. Then, the temperature was decreased to room temperature, and the reaction product was worked-up using dichloromethane and water. An organic layer was dried using anhydrous $Na_2SO_4$. The dried organic layer was filtered and additionally dried using a decompression apparatus to obtain 0.09 mol of thionated N,N-diethyl-3-butenethioamide represented by the following Formula 4-1:

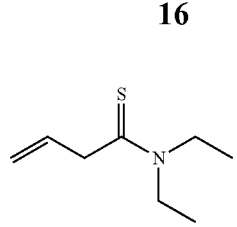

[Formula 4-1]

$^1$H NMR (CDCl$_3$, 500 MHz) δ 5.85-5.83 (m, 1H), 5.12-5.10 (m, 2H), 3.34 (d, 2H), 3.24 (q, 4H), 1.17 (t, 6H).

Hydrosilylation Reaction 0.09 mol of the prepared N,N-diethyl-3-butenethioamide was injected into a 1 L reactor which was purged with nitrogen, and 0.11 mol of triethoxysilane, and 0.004 mol of dicobalt octacarbonyl were injected thereto one by one. Then the temperature of the reactor was elevated to 40° C., followed by stirring for 6 hours. After completing hydrosilylation reaction, the temperature was decreased to room temperature, and the reaction product was worked-up using dichloromethane and water. An organic layer was dried using anhydrous $Na_2SO_4$. The dried product was separated by column chromatography via fluorous reverse-phase column (FPR) using acetonitrile as a developing solvent. Solvents were removed and dried using a decompression apparatus to obtain 0.08 mol of N,N-diethyl-4-(triethoxysilyl)butanethioamide represented by the following Formula 1-1:

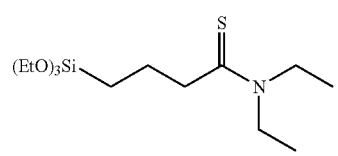

[Formula 1-1]

$^1$H NMR (CDCl$_3$, 500 MHz) δ 3.83 (q, 6H), 3.24 (q, 4H), 2.64 (t, 2H), 1.59 (t, 2H), 1.22 (t, 9H), 1.17 (t, 6H), 0.55 (t, 2H).

Preparation Example 2: Preparation of Compound of Formula 1-2 Below 0.09 mol of thionated 1-(piperidin-1-yl)-but-3-en-1-thione represented by Formula 4-2 below was obtained by conducting the same method as in Preparation Example 1 except for injecting 0.1 mol of 1-(piperidin-1-yl)-but-3-en-1-one instead of 0.1 mol of N,N-diethyl-3-butenamide in the thionation process of Preparation Example 1.

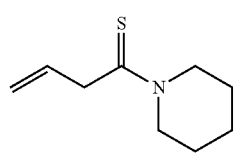

[Formula 4-2]

$^1$H NMR (CDCl$_3$, 500 MHz) δ 5.85-5.83 (m, 1H), 5.12-5.10 (m, 2H), 3.34 (d, 2H), 3.17-3.15 (m, 4H), 1.58-1.54 (m, 6H).

Then, 0.08 mol of 1-(piperidin-1-yl)-4-(triethoxysilyl)butane-1-thione represented by Formula 1-2 below was obtained by conducting the same method as in Preparation Example 1 except for injecting 0.09 mol of 1-(piperidin-1-yl)-but-3-en-1-thione obtained above instead of 0.09 mol of N,N-diethyl-3-butenethioamide in the hydrosilylation reaction of Preparation Example 1.

[Formula 1-2]

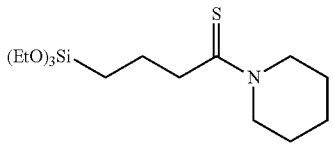

¹H NMR (CDCl₃, 500 MHz) δ 3.83 (q, 6H), 3.17-3.15 (m, 4H), 2.64 (t, 2H), 1.59 (t, 2H), 1.58-1.54 (m, 6H), 1.22 (t, 9H), 0.55 (t, 2H).

Preparation Example 3: Preparation of Compound of Formula 1-3 Below 0.08 mol of thionated 1-morpholinobut-3-en-1-thione represented by Formula 4-3 below was obtained by conducting the same method as in Preparation Example 1 except for injecting 0.1 mol of 1-morpholnobut-3-en-1-one instead of 0.1 mol of N,N-diethyl-3-butenamide in the thionation process of Preparation Example 1.

[Formula 4-3]

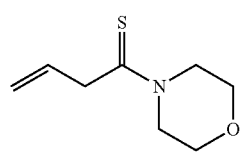

¹H NMR (CDCl₃, 500 MHz) δ 5.85-5.83 (m, 1H), 5.12-5.10 (m, 2H), 3.63 (t, 4H), 3.34 (d, 2H), 3.17 (t, 4H).

Then, 0.07 mol of 1-morpholino-4-(triethoxysilyl)butane-1-thione represented by Formula 1-3 below was obtained by conducting the same method as in Preparation Example 1 except for injecting 0.08 mol of 1-morpholinobut-3-en-1-thione obtained above instead of 0.09 mol of N,N-diethyl-3-butenethioamide in the hydrosilylation reaction of Preparation Example 1.

[Formula 1-3]

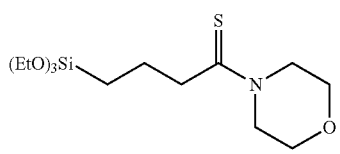

¹H NMR (CDCl₃, 500 MHz) δ 3.83 (q, 6H), 3.63 (t, 4H), 3.17 (t, 4H), 2.64 (t, 2H), 1.59 (t, 2H), 1.22 (t, 9H), 0.55 (t, 2H).

Preparation Example 4: Preparation of Compound of Formula 1-4 Below 0.07 mol of thionated 1-(4-methylpiperazin-1-yl)-but-3-en-1-thione represented by Formula 4-4 below was obtained by conducting the same method as in Preparation Example 1 except for injecting 0.1 mol of 1-(4-methylpiperazin-1-yl)-but-3-en-1-one instead of 0.1 mol of N,N-diethyl-3-butenamide in the thionation process of Preparation Example 1.

[Formula 4-4]

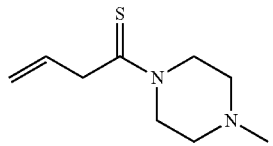

¹H NMR (CDCl₃, 500 MHz) δ 5.85-5.83 (m, 1H), 5.12-5.10 (m, 2H), 3.36 (t, 4H), 3.34 (d, 2H), 2.25 (t, 4H), 2.17 (s, 3H).

Then, 0.08 mol of 1-(4-methylpiperazin-1-yl)-4-(triethoxysilyl)butane-1-thione represented by Formula 1-4 below was obtained by conducting the same method as in Preparation Example 1 except for injecting 0.07 mol of 1-(4-methylpiperazin-1-yl)-but-3-en-1-thione obtained above instead of 0.09 mol of N,N-diethyl-3-butenethioamide in the hydrosilylation reaction of Preparation Example 1.

[Formula 1-4]

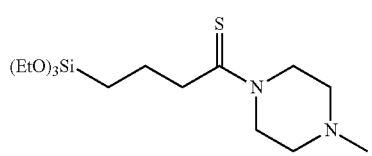

¹H NMR (CDCl₃, 500 MHz) δ 3.83 (q, 6H), 3.36 (t, 4H), 2.64 (t, 2H), 2.25 (t, 4H), 2.17 (s, 3H), 1.59 (t, 2H), 1.22 (t, 9H), 0.55 (t, 2H).

Preparation Example 5: Preparation of N,N-Dimethylvinylbenzylamine (Formula 2-1)

To a 500 ml round bottom flask which was purged with nitrogen, 150 ml of ethanol and 0.3 mol of 4-vinylbenzyl chloride were injected and the internal temperature was elevated to 70° C. while stirring. 0.35 mol of N,N-dimethylamine was slowly added dropwisely for 30 minutes. The reaction was conducted at 70° C. for 12 hours by stirring and the temperature was decreased to room temperature. After completing the reaction, the solution of the reaction product was removed under a reduced pressure, and a salt obtained was filtered to obtain 0.26 mol of N,N-dimethylvinylbenzylamine represented by the following Formula 2-1:

[Formula 2-1]

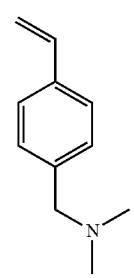

¹H NMR (CDCl₃, 500 MHz) δ 7.69 (d, 2H), 7.13 (d, 2H), 6.72 (dd, 1H), 5.76 (dd, 1H), 5.25 (dd, 1H), 3.68 (s, 2H), 2.17 (s, 6H).

EXAMPLES

Example 1

To a 20 L autoclave reactor, 315 g of styrene, 1,185 g of 1,3-butadiene, 7,500 g of n-hexane, and 3.0 g of tetramethylethylenediamine (TMEDA) as a polar additive were added, and the internal temperature of the reactor was elevated to 60° C. When the internal temperature of the reactor reached 60° C., 1.32 g of n-butyllithium was injected into the reactor as a polymerization initiator, and an adiabatic reaction with heating was performed. In this case, the internal temperature of the reactor was elevated to 80° C. by heat due to polymerization. After about 15 minutes from finishing the adiabatic reaction with the heat, 60 g of 1,3-butadiene was injected, and after 15 minutes, 40 mmol of N,N-diethyl-4-(triethoxysilyl)butanethioamide represented by Formula 1-1 and prepared in Preparation Example 1 as a modifier for modification reaction was injected, and reaction was conducted for 30 minutes. Then, the polymerization reaction was quenched by injecting 30 g of methanol, and 45 ml of a hexane solution in which 0.3 wt % of a butyrate hydroxytoluene (BHT) antioxidant was dissolved was added thereto. The polymer thus obtained was injected into hot water heated with steam, stirred to remove solvents, and roll dried to remove remaining solvents and water to prepare a modified and conjugated diene-based polymer. Analysis results of the modified and conjugated diene-based polymer thus prepared are shown in Table 1 below.

Example 2

The same method as in Example 1 was conducted except for injecting 41.5 mmol of 1-(piperidin-1-yl)-4-(triethoxysilyl)butane-1-thione represented by Formula 1-2 and prepared in Preparation Example 2 instead of 40 mmol of N,N-diethyl-4-(triethoxysilyl)butanethioamide represented by Formula 1-1 and prepared in Preparation Example 1 in Example 1.

Example 3

The same method as in Example 1 was conducted except for injecting 41.7 mmol of 1-morpholino-4-(triethoxysilyl)butane-1-thione represented by Formula 1-3 and prepared in Preparation Example 3 instead of 40 mmol of N,N-diethyl-4-(triethoxysilyl)butanethioamide represented by Formula 1-1 and prepared in Preparation Example 1 in Example 1.

Example 4

The same method as in Example 1 was conducted except for injecting 41.6 mmol of 1-(4-methylpiperazin-1-yl)-4-(triethoxysilyl)butane-1-thione represented by Formula 1-4 and prepared in Preparation Example 4 instead of 40 mmol of N,N-diethyl-4-(triethoxysilyl)butanethioamide represented by Formula 1-1 and prepared in Preparation Example 1 in Example 1.

Example 5

To a 20 L autoclave reactor, 315 g of styrene, 1,185 g of 1,3-butadiene, 7,500 g of n-hexane, 3.0 g of tetramethylethylenediamine (TMEDA) as a polar additive, and 6.64 g of N,N-dimethylvinylbenzylamine represented by Formula 2-1 and prepared in Preparation Example 5 were added, and the internal temperature of the reactor was elevated to 60° C. When the internal temperature of the reactor reached 60° C., 1.32 g of n-butyllithium was injected into the reactor as a polymerization initiator, and an adiabatic reaction with heating was performed. In this case, the internal temperature of the reactor was elevated to 80° C. by heat due to polymerization. After about 15 minutes from finishing the adiabatic reaction with the heat, 60 g of 1,3-butadiene was injected, and after 15 minutes, 40 mmol of N,N-diethyl-4-(triethoxysilyl)butanethioamide represented by Formula 1-1 and prepared in Preparation Example 1 was injected as a modifier for modification reaction, and reaction was conducted for 30 minutes. Then, the polymerization reaction was quenched by injecting 30 g of methanol, and 45 ml of a hexane solution in which 0.3 wt % of a butyrate hydroxytoluene (BHT) antioxidant was dissolved was added thereto. The polymer thus obtained was injected into hot water heated with steam and stirred to remove solvents, and roll dried to remove remaining solvents and water to prepare a modified and conjugated diene-based polymer. Analysis results of the modified and conjugated diene-based polymer thus prepared are shown in Table 1 below.

Example 6

The same method as in Example 5 was conducted except for injecting 41.5 mmol of 1-(piperidin-1-yl)-4-(triethoxysilyl)butane-1-thione represented by Formula 1-2 and prepared in Preparation Example 2 instead of 40 mmol of N,N-diethyl-4-(triethoxysilyl)butanethioamide represented by Formula 1-1 and prepared in Preparation Example 1 in Example 5.

Example 7

The same method as in Example 5 was conducted except for injecting 41.7 mmol of 1-morpholino-4-(triethoxysilyl)butane-1-thione represented by Formula 1-3 and prepared in Preparation Example 3 instead of 40 mmol of N,N-diethyl-4-(triethoxysilyl)butanethioamide represented by Formula 1-1 and prepared in Preparation Example 1 in Example 5.

Example 8

The same method as in Example 5 was conducted except for injecting 41.6 mmol of 1-(4-methylpiperazin-1-yl)-4-(triethoxysilyl)butane-1-thione represented by Formula 1-4 and prepared in Preparation Example 4 instead of 40 mmol of N,N-diethyl-4-(triethoxysilyl)butanethioamide represented by Formula 1-1 and prepared in Preparation Example 1 in Example 5.

Comparative Example 1

The same method as in Example 1 was conducted except for not injecting the compound represented by Formula 1-1 and prepared in Preparation Example 1 in Example 1.

Comparative Example 2

The same method as in Example 5 was conducted except for injecting 34.5 mmol of N,N-diethyl-3-(triethoxysilyl)propan-1-amine instead of the compound represented by Formula 1-1 and prepared in Preparation Example 1 in Example 5.

Comparative Example 3

The same method as in Example 5 was conducted except for not injecting the compound represented by Formula 1-1 and prepared in Preparation Example 1 in Example 5.

EXPERIMENTAL EXAMPLES

Experimental Example 1

A styrene unit and the vinyl content in a butadiene unit in each conjugated diene-based polymer, a weight average molecular weight (Mw, $\times 10^3$ g/mol), a number average molecular weight (Mn, $\times 10^3$ g/mol), molecular weight distribution (WMD), and mooney viscosity (MV) were measured for each of the modified or unmodified conjugated diene-based polymers prepared in the examples and the comparative examples. The results are shown in Table 1 below.

The styrene unit (SM, wt %), the butadiene unit (BD, wt %) and the vinyl content (Vinyl, wt %) in the conjugated diene-based polymer were measured and analyzed using Varian VNMRS 500 MHz NMR.

The weight average molecular weight (Mw) and the number average molecular weight (Mn) were measured by gel permeation chromatography (GPC) analysis and the molecular weight distribution (MWD, Mw/Mn) was obtained by calculating using each of the measured molecular weights. Particularly, GPC used two columns of PLgel Olexis (Polymer Laboratories Co. Ltd.) and one column of PLgel mixed-C (Polymer Laboratories Co. Ltd.) in combination, and newly replaced columns were all mixed bed type columns. Polystyrene (PS) was used as a GPC standard material for calculating the molecular weights.

The mooney viscosity (MV, (ML1+4, @100° C.) MU) was measured by using MV-2000 (Alpha Technologies Co., Ltd.) at 100° C. using Large Rotor at a rotor speed of 2±0.02 rpm. In this case, a specimen used was stood at room temperature (23±3° C.) for 30 minutes or more, and 27±3 g of the specimen was collected and put in a die cavity, and then, Platen was operated for 4 minutes for measurement.

material rubber. In this case, the raw material rubber is a rubber including 70 wt % of each modified or unmodified conjugated diene-based polymer of the examples and comparative examples and 30 wt % of polybutadiene (BR).

TABLE 2

| Division | Raw material | Amount (parts by weight) |
|---|---|---|
| First stage mulling | Rubber (SSBR 70 wt % + BR 30 wt %) | 100 |
| | Process oil (TDAE) | 40 |
| | Silica (Degussa 7000GR) | 95 |
| | Coupling agent/carbon black (Degussa Z50S, 50 wt % carbon black and 50 wt % bis (3-triethoxysilylpropyltetrasulfane) | 11.2 |
| | Stearic acid | 2 |
| | Zinc white (ZnO) | 3 |
| | Antioxidant (Flexsys, polymerized 2,2,4-trimethyl-1,2-dihydroquinoline) | 2 |
| | Antiaging agent (Flexsys, N-1,3-dimethylbutyl-N'-phenyl-p-phenylenediamine) | 2 |
| | Wax | 1 |
| Second stage mulling | Sulfur | 1.5 |
| | Fist vulcanization accelerator (Flexsys, diphenylguanidine) | 1.75 |
| | Second vulcanization accelerator (Flexsys, N-t-butyl-2-benzothiazyl sulfonamide) | 2 |

Particularly, the rubber specimen was mulled via a first stage mulling and a second stage mulling. In the first stage mulling, a raw material rubber (a styrene-butadiene copolymer and polybutadiene), a process oil, a silica filler, a coupling agent/carbon black, stearic acid, zinc white, an antioxidant, an antiaging agent, and wax were mulled by using a banbury mixer equipped with a temperature controlling apparatus. In this case, the revolution number of a rotor was increased, and the temperature of a mulling apparatus was controlled to 150° C. When the temperature reached 150° C., the rpm of the rotor was controlled and kept for 5 minutes to keep the temperature, and the first mulling

TABLE 1

| | Example | | | | | | | | Comparative Example | | |
|---|---|---|---|---|---|---|---|---|---|---|---|
| Division | 1 | 2 | 3 | 4 | 5 | 6 | 7 | 8 | 1 | 2 | 3 |
| SM (wt %) | 33.0 | 33.0 | 33.1 | 33.2 | 33.2 | 33.1 | 33.0 | 33.3 | 33.3 | 33.0 | 33.2 |
| Vinyl (wt %) | 40.4 | 40.7 | 40.8 | 40.9 | 40.7 | 41.0 | 40.9 | 41.0 | 41.0 | 40.2 | 40.5 |
| Mw ($\times 10^3$ g/mol) | 498 | 500 | 495 | 496 | 504 | 511 | 508 | 506 | 465 | 501 | 470 |
| Mn ($\times 10^3$ g/mol) | 313 | 311 | 310 | 309 | 320 | 330 | 325 | 323 | 300 | 333 | 303 |
| MWD (Mw/Mn) | 1.55 | 1.54 | 1.53 | 1.56 | 1.57 | 1.54 | 1.55 | 1.57 | 1.51 | 1.68 | 1.50 |
| MV | 66 | 65 | 65 | 64 | 67 | 69 | 67 | 68 | 59 | 65 | 61 |

Experimental Example 2

In order to comparatively analyze the physical properties of a rubber composition including each modified or unmodified conjugated diene-based copolymer of the examples and comparative examples, and a molded article manufactured therefrom, tensile properties, abrasion resistance and wet traction were measured. The results are shown in Table 4 and Table 5 below.

1) Preparation of Rubber Specimen

Mixing was conducted with mixing conditions shown in Table 2 below based on 100 parts by weight of a raw was conducted to obtain a first compound mixture. In the second stage mulling, sulfur and a vulcanization accelerator were added to the first compound mixture, mixing was softly conducted at the temperature of 50° C. for 1.5 minutes with the revolution speed of the rotor of 50 rpm, and a sheet was manufactured in a roll of 50° C. to obtain a second compound mixture. Via a press work of the compounding completed specimens at 160° C. for the time of 1.3 times T90 which was a crosslinking rate among measured MDR data at 160° C., crosslinked specimens for measuring mechanical properties and rheolosy were manufactured.

TABLE 3

| Division | Example 1 | 2 | 3 | 4 | 5 | 6 | 7 | 8 | Comparative Example 1 | 2 | 3 |
|---|---|---|---|---|---|---|---|---|---|---|---|
| Tmin (N·M) | 4.1 | 3.9 | 4.0 | 4.2 | 4.1 | 4.0 | 4.2 | 4.3 | 4.0 | 3.9 | 4.5 |
| Tmax (N·M) | 28.0 | 29.2 | 29.0 | 29.4 | 29.0 | 30.0 | 29.5 | 30.5 | 24.7 | 27.1 | 25.1 |
| T90 (min) | 18.0 | 18.2 | 18.1 | 18.3 | 18.1 | 18.5 | 18.4 | 18.0 | 16.2 | 17.8 | 16.5 |

2) Tensile Properties

The tensile properties were measured by manufacturing each specimen and measuring tensile strength when broken, tensile stress when elongated by 300% (300% modulus), and elongation of each specimen according to an ASTM 412 tensile test method. Particularly, tensile properties were measured using a Universal Test machine 4204 tensile tester (Instron Co., Ltd.) at room temperature at a rate of 50 cm/min. The index of the tensile stress when elongated by 300% (300% modulus) was represented based on the value of the tensile stress when elongated by 300% (300% modulus) of Comparative Example 2.

3) Glass Transition Temperature (Tg)

Glass transition temperature was measured using a differential scanning calorimeter (DSC) apparatus (Perkin-Elmer Co., Ltd.), and a mid-point method was used as a method for measuring the glass transition temperature (Tg) of a specimen. In order to prevent the decomposition of a polymer specimen, measurement was conducted under a nitrogen atmosphere, and about 5-20 mg of the specimen was used for the measurement.

4) Viscoelasticity Properties

The viscoelasticity properties were measured by using a dynamic mechanical analyzer (TA Co., Ltd.). Tan δ was measured by changing deformation at each measurement temperature (−60° C. to 60° C.) with a twist mode and a frequency of 10 Hz. If the tan δ at a low temperature of 0° C. is high, it means that wet traction is good, and if the tan δ at a high temperature of 60° C. is low, it means that hysteresis loss is small, and low rolling resistance (fuel consumption ratio) is good. The indexes of tan δ at 0° C. and tan δ at 60° C. are respectively shown based on the values of tan δ at 0° C. and tan δ at 60° C. of Comparative Example 2.

TABLE 5

| | Division | Comparative Example 1 | 2 | 3 |
|---|---|---|---|---|
| Tensile properties | 300% modulus (kgf/cm$^2$) | 98 | 110 | 100 |
| | 300% modulus index | 89 | 100 | 91 |
| | Tensile strength (kgf/cm$^2$) | 171 | 180 | 170 |
| | Elongation (%) | 401 | 415 | 400 |
| Viscoelasticity properties | Glass transition temperature | −18.6 | −18.5 | −18.7 |
| | tan δ @0° C. | 0.368 | 0.383 | 0.370 |
| | tan δ @0° C. index | 96 | 100 | 97 |
| | tan δ @60° C. | 0.198 | 0.181 | 0.196 |
| | tan δ @60° C. index | 91 | 100 | 92 |

As shown in Table 4 and Table 5, the modified and conjugated diene-based polymers of Examples 1 to 4 prepared according to the present invention were secured to have markedly improved 300% modulus, increased tensile strength and elongation and excellent tensile properties, increased tan δ at a low temperature of 0° C. and excellent wet traction, and increased tan δ at a high temperature of 60° C. and a small hysteresis loss and excellent low running resistance (fuel consumption ratio) when compared to Comparative Example 1 in which a modification reaction was not conducted.

Also, the modified and conjugated diene-based polymers of Examples 5 to 8 including a repeating unit derived from a modification monomer together with a functional group derived from a modifier according to the present invention were secured to have markedly improved 300% modulus, increased tan δ at a high temperature of 60° C. and a small hysteresis loss and excellent low running resistance (fuel

TABLE 4

| | Division | Example 1 | 2 | 3 | 4 | 5 | 6 | 7 | 8 |
|---|---|---|---|---|---|---|---|---|---|
| Tensile properties | 300% modulus (kgf/cm$^2$) | 123 | 125 | 124 | 126 | 125 | 127 | 127 | 129 |
| | 300% modulus index | 112 | 114 | 113 | 115 | 114 | 115 | 115 | 117 |
| | Tensile strength (kgf/cm$^2$) | 175 | 178 | 179 | 174 | 177 | 175 | 178 | 180 |
| | Elongation (%) | 404 | 405 | 403 | 404 | 405 | 408 | 407 | 406 |
| Viscoelasticity properties | Glass transition temperature (° C.) | −18.8 | −18.6 | −18.9 | −18.8 | −19 | −18.9 | −18.8 | −19.0 |
| | tan δ @0° C. | 0.380 | 0.383 | 0.384 | 0.381 | 0.381 | 0.384 | 0.385 | 0.384 |
| | tan δ @0° C. index | 99 | 100 | 100 | 99 | 99 | 100 | 101 | 100 |
| | tan δ @60° C. | 0.165 | 0.164 | 0.162 | 0.166 | 0.163 | 0.162 | 0.160 | 0.158 |
| | tan δ @60° C. index | 110 | 110 | 112 | 109 | 111 | 112 | 113 | 115 | consumption ratio) when compared to Comparative Example 2 which was modified from a modifier not including a thioamide group in a molecule and Comparative Example 3 in which a modification reaction was not conducted.

From the above results, it may be found that if a conjugated diene-based polymer is modified from a modifier including a thioamide functional group which has excellent hydrophilicity in a molecule according to the present invention, and thus has excellent affinity with an inorganic filler, the functional group derived from the modifier is included at one terminal of the polymer, and a modified and conjugated diene-based polymer having excellent affinity with an inorganic filler may be prepared, and thus, the modified and conjugated diene-based polymer thus prepared has excellent tensile properties and viscoelasticity properties.

The invention claimed is:

1. A modified and conjugated diene-based polymer comprising a repeating unit derived from a conjugated diene-based monomer and a functional group derived from a modifier comprising a compound represented by the following Formula 1 at one terminal of the polymer:

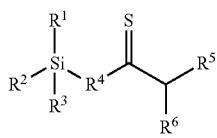

[Formula 1]

in Formula 1,

R$^1$ to R$^3$ are each independently a monovalent hydrocarbon group of 1 to 30 carbon atoms, a heteroalkyl group of 1 to 30 carbon atoms, or a heterocyclic group of 3 to 30 carbon atoms, where at least one of R$^1$ to R$^3$ is the heteroalkyl group of 1 to 30 carbon atoms, or the heterocyclic group of 3 to 30 carbon atoms, R$^4$ is a divalent hydrocarbon group of 1 to 30 carbon atoms, R$^5$ and R$^6$ are each independently a monovalent hydrocarbon group of 1 to 30 carbon atoms, or R$^5$ and R$^6$ are combined with each other to form a saturated or unsaturated cyclic structure of 3 to 20 carbon atoms together with an adjacent N atom, where in case R$^5$ and R$^6$ form a cyclic structure, at least one heteroatom selected from the group consisting of O and S or NR$^{13}$ may be included, and R$^{13}$ is a monovalent hydrocarbon group of 1 to 30 carbon atoms, or a silyl group which is mono-, di- or tri-substituted with a monovalent hydrocarbon group of 1 to 30 carbon atoms.

2. A modified and conjugated diene-based polymer comprising a repeating unit derived from a conjugated diene-based monomer and a repeating unit derived from a modification monomer comprising a compound represented by the following Formula 2, and comprising a functional group derived from a modifier comprising a compound represented by the following Formula 1 at one terminal of the polymer:

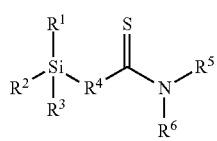

[Formula 1]

in Formula 1,

R$^1$ to R$^3$ are each independently a monovalent hydrocarbon group of 1 to 30 carbon atoms, a heteroalkyl group of 1 to 30 carbon atoms, or a heterocyclic group of 3 to 30 carbon atoms, where at least one of R$^1$ to R$^3$ is the heteroalkyl group of 1 to 30 carbon atoms, or the heterocyclic group of 3 to 30 carbon atoms, R$^4$ is a divalent hydrocarbon group of 1 to 30 carbon atoms, R$^5$ and R$^6$ are each independently a monovalent hydrocarbon group of 1 to 30 carbon atoms, or R$^5$ and R$^6$ are combined with each other to form a saturated or unsaturated cyclic structure of 3 to 20 carbon atoms together with an adjacent N atom, where in case R$^5$ and R$^6$ form a cyclic structure, at least one heteroatom selected from the group consisting of O and S or NR$^{13}$ may be included, and R$^{13}$ is a monovalent hydrocarbon group of 1 to 30 carbon atoms, or a silyl group which is mono-, di- or tri-substituted with a monovalent hydrocarbon group of 1 to 30 carbon atoms,

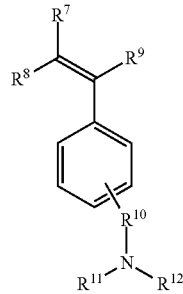

[Formula 2]

in Formula 2,

R$^7$, R$^8$ and R$^9$ are each independently hydrogen or a monovalent hydrocarbon group of 1 to 20 carbon atoms, R$^{10}$ is a single bond, a divalent hydrocarbon group of 1 to 20 carbon atoms, or a hetero alkylene group containing at least one heteroatom selected from the group consisting of O and S or NR$^{14}$, R$^{11}$ and R$^{12}$ are each independently a monovalent hydrocarbon group of 1 to 30 carbon atoms, or a silyl group which is mono-, di- or tri-substituted with a monovalent hydrocarbon group of 1 to 30 carbon atoms, or R$^{11}$ and R$^{12}$ are combined with each other to form a saturated or unsaturated cyclic structure of 3 to 20 carbon atoms together with an adjacent N atom, where in case R$^{11}$ and R$^{12}$ form a cyclic structure, at least one heteroatom selected from the group consisting of O and S or NR$^{15}$ may be included, and R$^{14}$ and R$^{15}$ are each independently a monovalent hydrocarbon group of 1 to 30 carbon atoms, or a silyl group which is mono-, di- or tri-substituted with a monovalent hydrocarbon group of 1 to 30 carbon atoms.

3. The modified and conjugated diene-based polymer of claim 1, wherein in Formula 1, R$^1$ to R$^3$ are each independently a monovalent hydrocarbon group of 1 to 20 carbon atoms, a heteroalkyl group of 1 to 20 carbon atoms, or a heterocyclic group of 3 to 20 carbon atoms, where at least one of R$^1$ to R$^3$ is the heteroalkyl group of 1 to 20 carbon atoms, or the heterocyclic group of 3 to 20 carbon atoms, $R^4$ is a divalent hydrocarbon group of 1 to 20 carbon atoms, $R^5$ and $R^6$ are each independently a monovalent hydrocarbon group of 1 to 12 carbon atoms, or $R^5$ and $R^6$ are combined with each other to form a saturated or unsaturated cyclic structure of 3 to 12 carbon atoms together with an adjacent N atom, where in case $R^5$ and $R^6$ form a cyclic structure, at least one heteroatom selected from the group consisting of O and S or $NR^{13}$ may be included, and $R^{13}$ is a monovalent hydrocarbon group of 1 to 12 carbon atoms, or a silyl group which is mono-, di- or tri-substituted with a monovalent hydrocarbon group of 1 to 12 carbon atoms.

4. The modified and conjugated diene-based polymer of claim 1, wherein the compound represented by Formula 1 is at least one selected from compounds represented by the following Formulae 1-1 to 1-4:

[Formula 1-1]

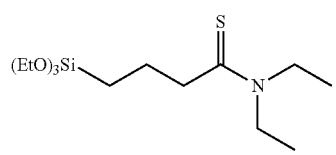

[Formula 1-2]

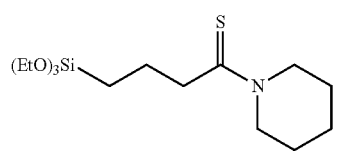

[Formula 1-3]

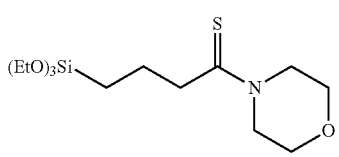

[Formula 1-4]

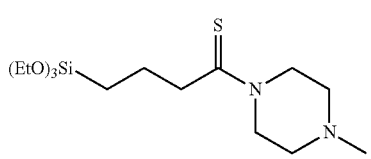

in Formulae 1-1 to 1-4, Et is an ethyl group.

5. The modified and conjugated diene-based polymer of claim 2, wherein the compound represented by Formula 2 is at least one selected from the group consisting of N,N-dimethylvinylbenzylamine, N,N-diethylvinylbenzylamine, N,N-dipropylvinylbenzylamine, N,N-dibutylvinylbenzylamine, N,N-diphenylvinylbenzylamine, 2-dimethylaminoethylstyrene, 2-diethylaminoethylstyrene, 2-bis(trimethylsilyl)aminoethylstyrene, 1-(4-N,N-dimethylaminophenyl)-1-phenylethylene, N,N-dimethyl-2-(4-vinylbenzyloxy)ethylamine, N,N,N'-trimethyl-N'-(4-vinylbenzyl)ethane-1,2-diamine, N,N-dimethyl-2-((4-vinylbenzyl)thio)ethylamine, 4-(2-pyrrolidinoethyl) styrene, 4-(2-piperidinoethyl)styrene, 4-(2-hexamethyleneiminoethyl)styrene, 4-(2-morpholinoethyl)styrene, 4-(2-thiaminoethyl)styrene, 4-(2-N-methylpiperazinoethyl)styrene, 1-((4-vinylphenoxy)methyl)pyrrolidine, 1-(4-vinylbenzyloxymethyl)pyrrolidine, 1-((4-vinylbenzyl)thiomethyl)pyrrolidine, and N-methyl-1-(pyrrolidine-1-yl)-N-(4-vinylbenzyl)methylamine.

6. The modified and conjugated diene-based polymer of claim 1, wherein the modified and conjugated diene-based polymer further comprises a repeating unit derived from an aromatic vinyl monomer.

7. The modified and conjugated diene-based polymer of claim 1, wherein the modified and conjugated diene-based polymer has a number average molecular weight (Mn) of 10,000 g/mol to 2,000,000 g/mol.

8. The modified and conjugated diene-based polymer of claim 1, wherein the modified and conjugated diene-based polymer has molecular weight distribution (Mw/Mn) of 1 to 5.

9. A method for preparing a modified and conjugated diene-based polymer, the method comprising:

a step of polymerizing conjugated diene-based monomers, or an aromatic vinyl-based monomer and a conjugated diene-based monomer in the presence of an organometal compound in a hydrocarbon solvent to prepare an active polymer which is combined with an organometal (S1); and a step of reacting the active polymer with a modifier comprising a compound represented by the following Formula 1 (S2):

[Formula 1]

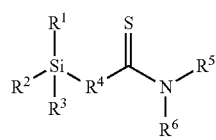

in Formula 1, $R^1$ to $R^3$ are each independently a monovalent hydrocarbon group of 1 to 30 carbon atoms, a heteroalkyl group of 1 to 30 carbon atoms, or a heterocyclic group of 3 to 30 carbon atoms, where at least one of $R^1$ to $R^3$ is the heteroalkyl group of 1 to 30 carbon atoms, or the heterocyclic group of 3 to 30 carbon atoms, $R^4$ is a divalent hydrocarbon group of 1 to 30 carbon atoms, $R^5$ and $R^6$ are each independently a monovalent hydrocarbon group of 1 to 30 carbon atoms, or $R^5$ and $R^6$ are combined with each other to form a saturated or unsaturated cyclic structure of 3 to 20 carbon atoms together with an adjacent N atom, where in case $R^5$ and $R^6$ form a cyclic structure, at least one heteroatom selected from the group consisting of O and S or $NR^{13}$ may be included, and $R^{13}$ is a monovalent hydrocarbon group of 1 to 30 carbon atoms, or a silyl group which is mono-, di- or tri-substituted with a monovalent hydrocarbon group of 1 to 30 carbon atoms.

10. The method for preparing a modified and conjugated diene-based polymer of claim 9, wherein the polymerizing in step (S1) is conducted by comprising a modification monomer containing a compound represented by the following Formula 2:

[Formula 2]

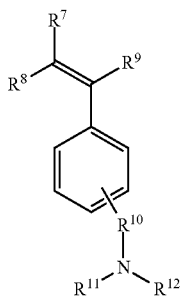

in Formula 2, $R^7$, $R^8$ and $R^9$ are each independently hydrogen or a monovalent hydrocarbon group of 1 to 20 carbon atoms, $R^{10}$ is a single bond, a divalent hydrocarbon group of 1 to 20 carbon atoms, or a hetero alkylene group containing at least one heteroatom selected from the group consisting of O and S or $NR^{14}$, $R^{11}$ and $R^{12}$ are each independently a monovalent hydrocarbon group of 1 to 30 carbon atoms, or a silyl group which is mono-, di- or tri-substituted with a monovalent hydrocarbon group of 1 to 30 carbon atoms, or $R^{11}$ and $R^{12}$ are combined with each other to form a saturated or unsaturated cyclic structure of 3 to 20 carbon atoms together with an adjacent N atom, wherein in case $R^{11}$ and $R^{12}$ form a cyclic structure, at least one heteroatom selected from the group consisting of O and S or $NR^{15}$ may be included, and $R^{14}$ and $R^{15}$ are each independently a monovalent hydrocarbon group of 1 to 30 carbon atoms, or a silyl group which is mono-, di- or tri-substituted with a monovalent hydrocarbon group of 1 to 30 carbon atoms.

11. The method for preparing a modified and conjugated diene-based polymer of claim 9, wherein the organometal compound is used in an amount of 0.01 mmol to 10 mmol based on 100 g of a total amount of the monomers.

12. The method for preparing a modified and conjugated diene-based polymer of claim 9, wherein the organometal compound is at least one selected from the group consisting of methyllithium, ethyllithium, propyllithium, n-butyllithium, s-butyllithium, t-butyllithium, hexyllithium, n-decyllithium, t-octyllithium, phenyllithium, 1-naphthyl lithium, n-eicosyl lithium, 4-butylphenyl lithium, 4-tolyl lithium, cyclohexyl lithium, 3,5-di-n-heptylcyclohexyl lithium, 4-cyclopentyl lithium, naphthyl sodium, naphthyl potassium, lithium alkoxide, sodium alkoxide, potassium alkoxide, lithium sulfonate, sodium sulfonate, potassium sulfonate, lithium amide, sodium amide, potassium amide, and lithium isopropylamide.

13. The method for preparing a modified and conjugated diene-based polymer of claim 9, wherein the polymerizing in step (S1) is conducted by comprising a polar additive.

14. The method for preparing a modified and conjugated diene-based polymer of claim 13, wherein the polar additive is at least one selected from the group consisting of tetrahydrofuran, ditetrahydrofurylpropane, diethyl ether, cycloamal ether, dipropyl ether, ethylene dimethyl ether, diethyl glycol, dimethyl ether, tert-butoxy ethoxy ethane, bis(3-dimethylaminoethyl) ether, (dimethylaminoethyl) ethyl ether, trimethylamine, triethylamine, tripropylamine, and tetramethylethylenediamine.

\* \* \* \* \*